US010219733B2

(12) United States Patent
Shimokawa et al.

(10) Patent No.: US 10,219,733 B2
(45) Date of Patent: Mar. 5, 2019

(54) PORTABLE URINE FLOW METER INCLUDING A GUIDE ARRANGED IN A NOZZLE PART IN A URINE FLOW PASSAGE TUBE

(71) Applicant: GEO SYSTEMS CO., LTD., Yokohama-shi, Kanagawa (JP)

(72) Inventors: Saburo Shimokawa, Yokohama (JP); Hiroshi Udagawa, Yokohama (JP); Tomomi Hara, Yokohama (JP); Rikio Kuragane, Yokohama (JP)

(73) Assignee: GEO SYSTEM CO., LTD., Yokohama-shi (JP)

( * ) Notice: Subject to any disclaimer, the term of this patent is extended or adjusted under 35 U.S.C. 154(b) by 150 days.

(21) Appl. No.: 15/316,977

(22) PCT Filed: Mar. 22, 2016

(86) PCT No.: PCT/JP2016/058966
§ 371 (c)(1),
(2) Date: Dec. 7, 2016

(87) PCT Pub. No.: WO2016/152847
PCT Pub. Date: Sep. 29, 2016

(65) Prior Publication Data
US 2017/0135622 A1 May 18, 2017

(30) Foreign Application Priority Data
Mar. 23, 2015 (JP) .................................. 2015-059524

(51) Int. Cl.
*A61B 5/20* (2006.01)
*G01F 1/075* (2006.01)
*A61B 5/00* (2006.01)

(52) U.S. Cl.
CPC .............. *A61B 5/208* (2013.01); *G01F 1/075* (2013.01); *A61B 5/6891* (2013.01)

(58) Field of Classification Search
None
See application file for complete search history.

(56) References Cited

U.S. PATENT DOCUMENTS 4,187,722 A   2/1980  Layton
4,557,274 A * 12/1985 Cawood ............... A61B 10/007
                                                                600/573

(Continued)

FOREIGN PATENT DOCUMENTS

JP    7-209055 A    8/1995
JP    2005-77402 A  3/2005

(Continued)

OTHER PUBLICATIONS

International Search Report dated Jun. 28, 2016, issued in counterpart International Application No. PCT/JP2016/058966 (2 pages).

(Continued)

*Primary Examiner* — Harshad R Patel
(74) *Attorney, Agent, or Firm* — Westerman, Hattori, Daniels & Adrian, LLP

(57) ABSTRACT

In this urine flow meter, a water wheel which is caused to rotate by a flow of urine from a urine flow passage tube is provided at a lower end side of the urine flow passage tube. The shape of a tip portion of the urine flow passage tube that causes urine to hit on the water wheel constitutes a nozzle part in which the tip-side is acutely processed, and an opening is formed in a sidewall surface of the tip-side. A guide is provided in a urine flow passage and is disposed in such a way that a tip of the guide is elongated as far as a tip-side region of the mine flow passage tube. The water wheel is caused to rotate by the flow of urine, and the urine (Continued)

flow rate can be detected on the basis of the rotation detection information.

7 Claims, 13 Drawing Sheets

(56) References Cited

U.S. PATENT DOCUMENTS

| | | | |
|---|---|---|---|
| 2005/0256428 A1* | 11/2005 | Aundal | A61B 5/208 600/574 |
| 2014/0296746 A1 | 10/2014 | Whitaker et al. | |

FOREIGN PATENT DOCUMENTS

| | | |
|---|---|---|
| JP | 2007-108085 A | 4/2007 |
| JP | 2009-84821 A | 4/2009 |
| JP | 2015-105948 A | 6/2015 |
| WO | 2007/079942 A1 | 7/2007 |
| WO | 2009/094761 A1 | 8/2009 |

OTHER PUBLICATIONS

Uchiyama et al., "Evaluation of Dynamic Performance of Tangential Flow Impeller-Type Flow Meter and Analysis of Causes of Occurrence of Metric Error", NII-Electronic Library Service, Jun. 1990, No. 43, pp. 67-74, w/English abstract (9 pages).
Fukutomi et al., "A study of a Cross-Flow Turbine", NII-Electronic Library Service, Jan. 1986, vol. 52, No. 473, pp. 407-411, w/English abstract (6 pages).
Extended (supplementary) European Search Report dated Oct. 2, 2018, issued in counterpart European Application No. 16768750.8. (6 pages).
Office Action dated Oct. 16, 2018, issued in counterpart Japanese Application No. 2017-508353, with English machine translation. (5 pages).

* cited by examiner

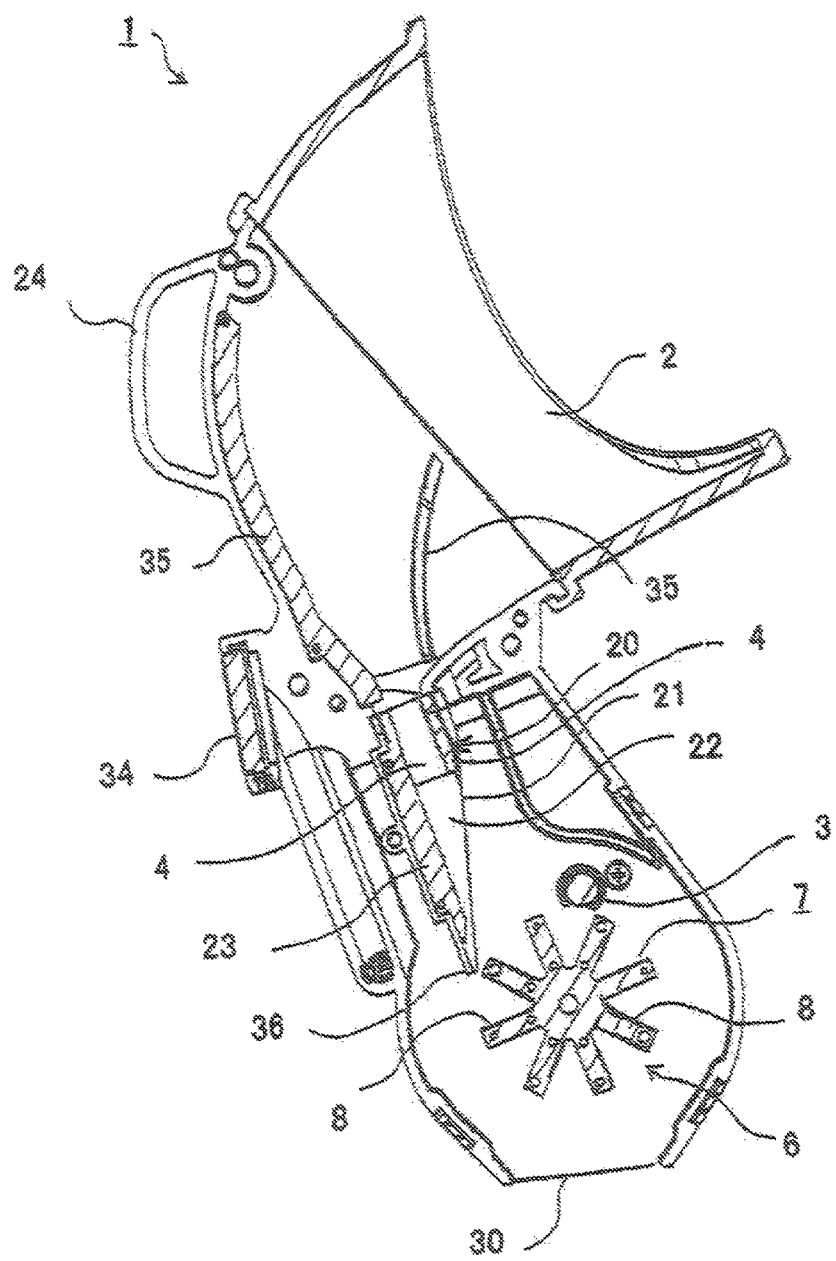
[Fig. 1]

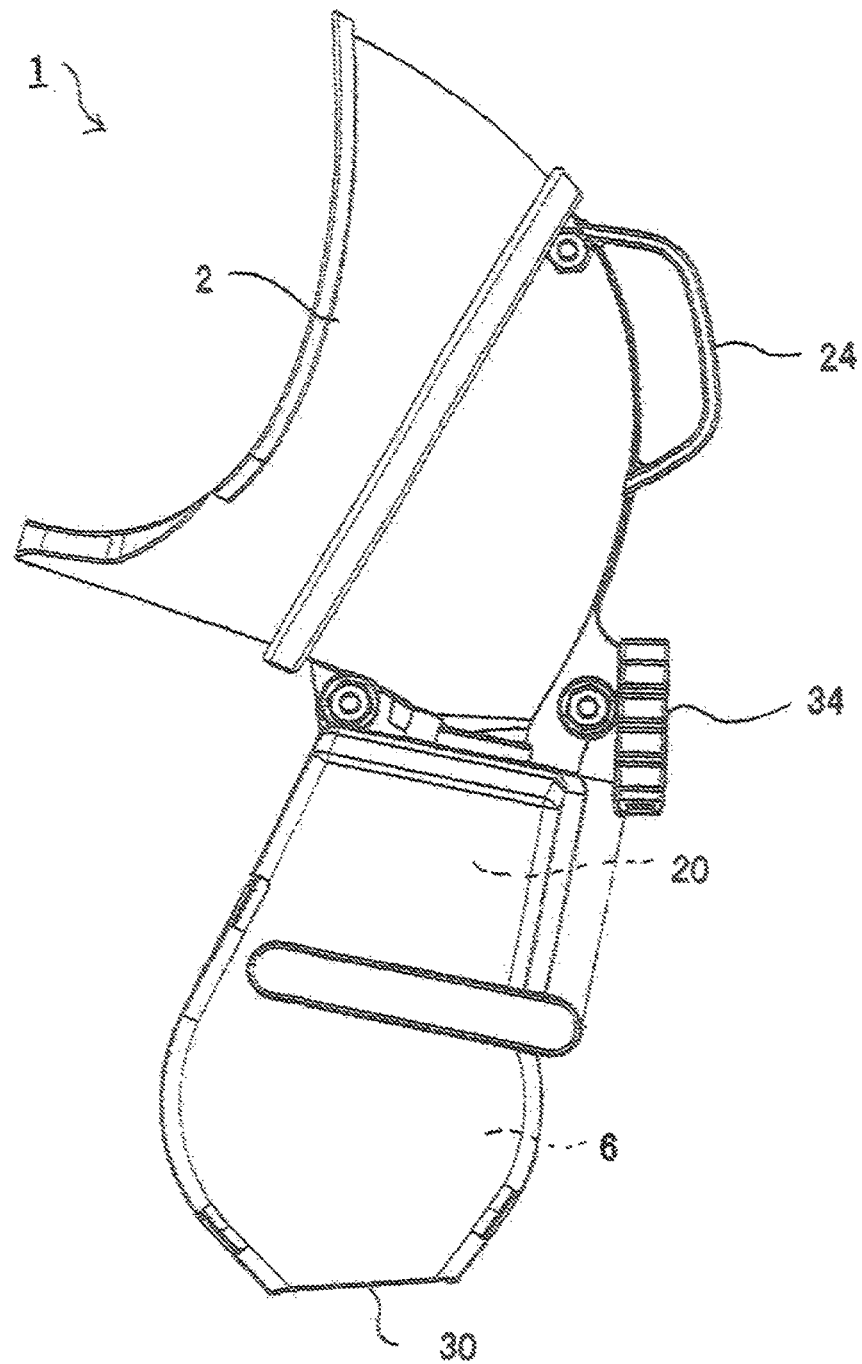
[Fig. 2]

[Fig. 3]
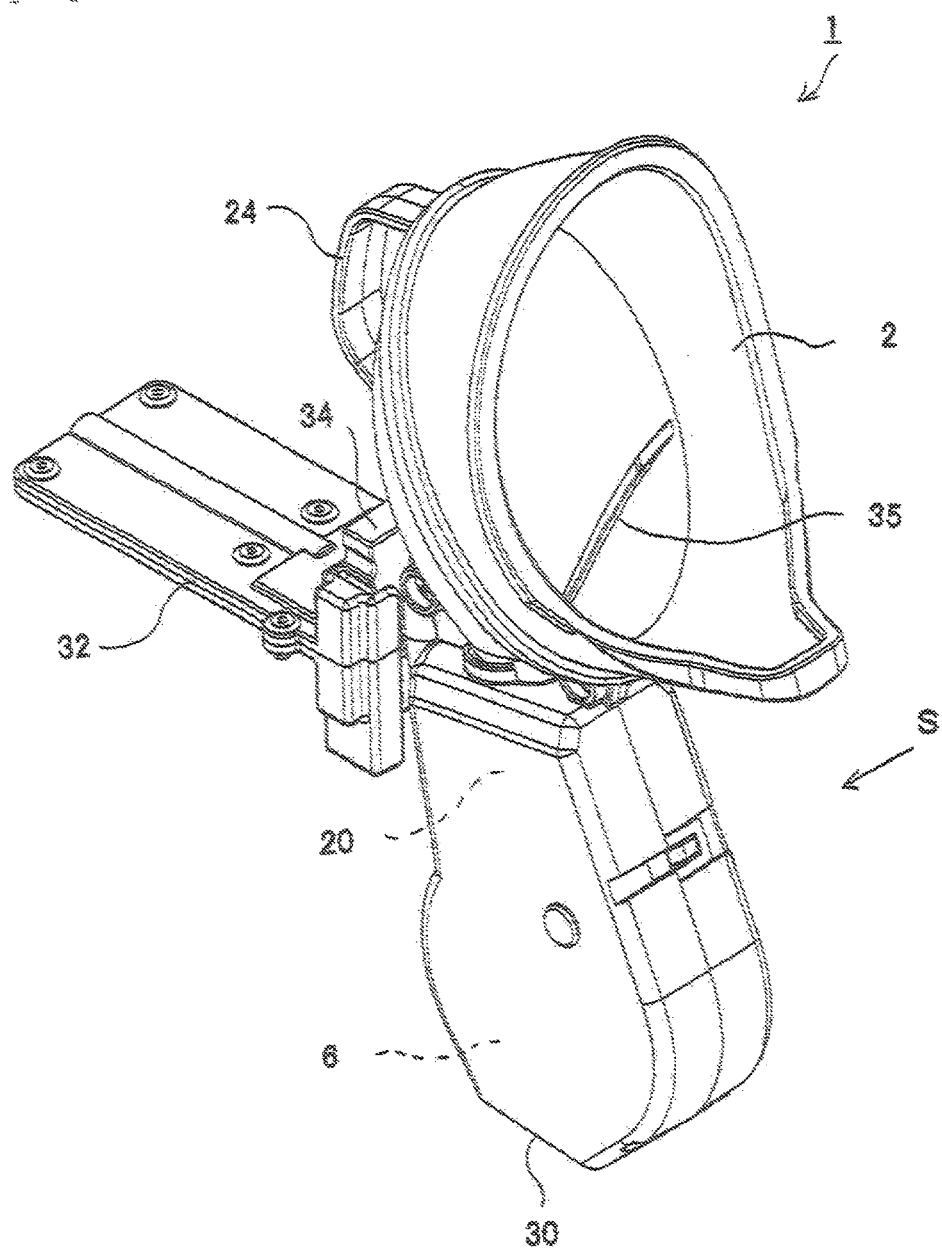

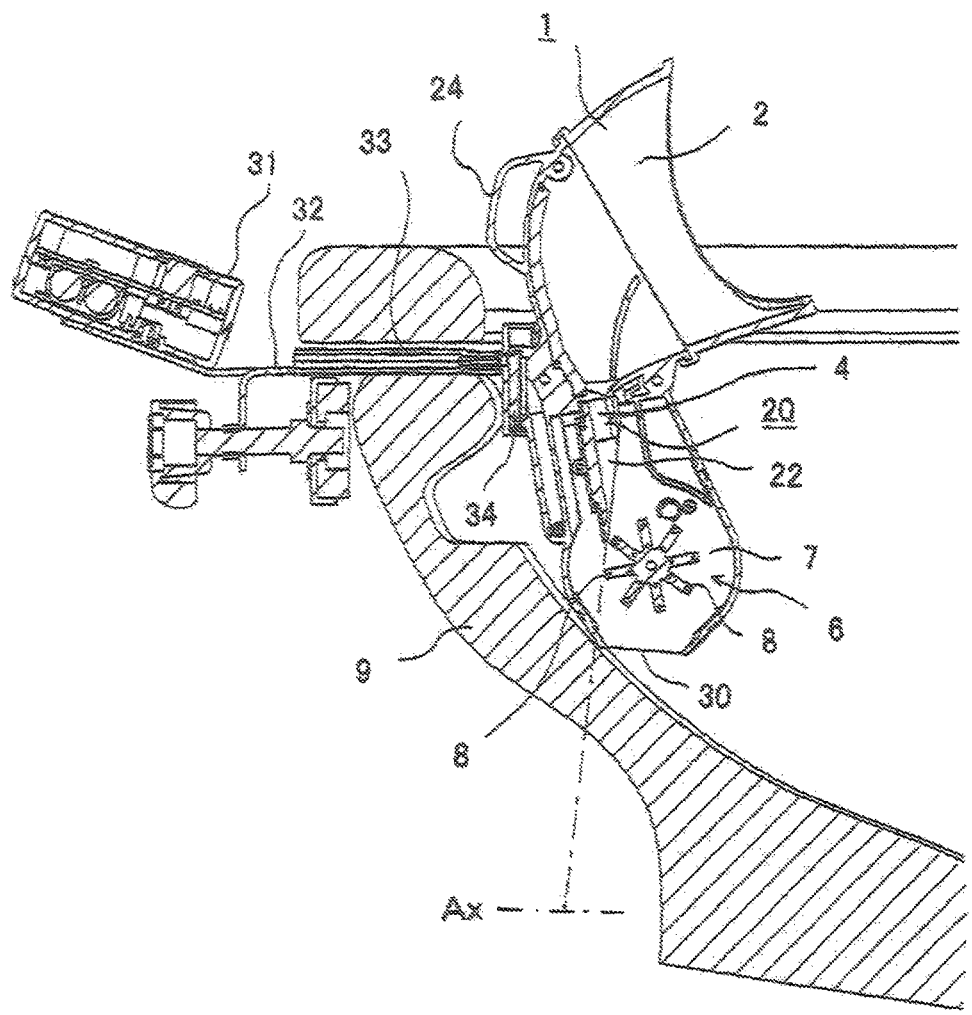
[Fig. 4]

[Fig. 5]
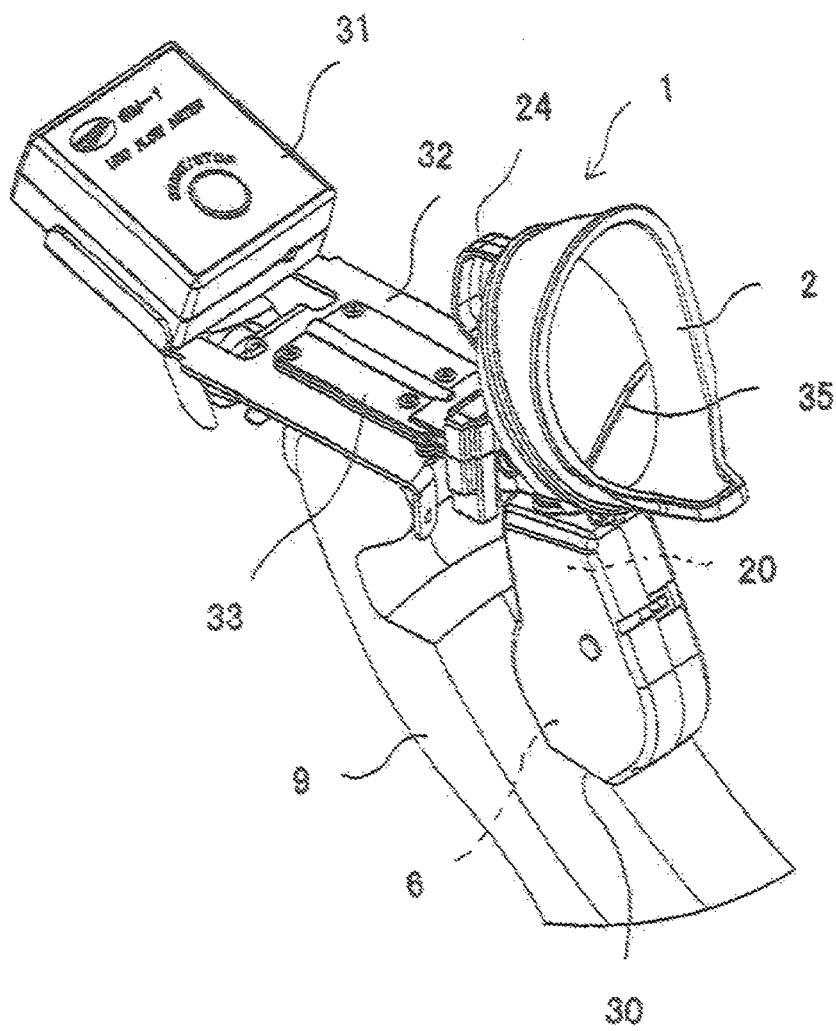
[Fig. 6]
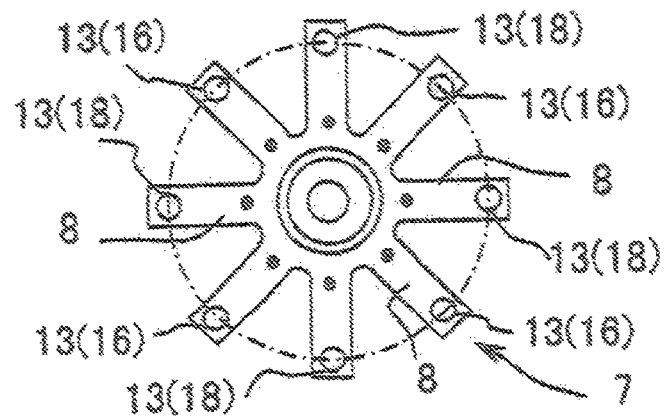

[Fig. 7a]
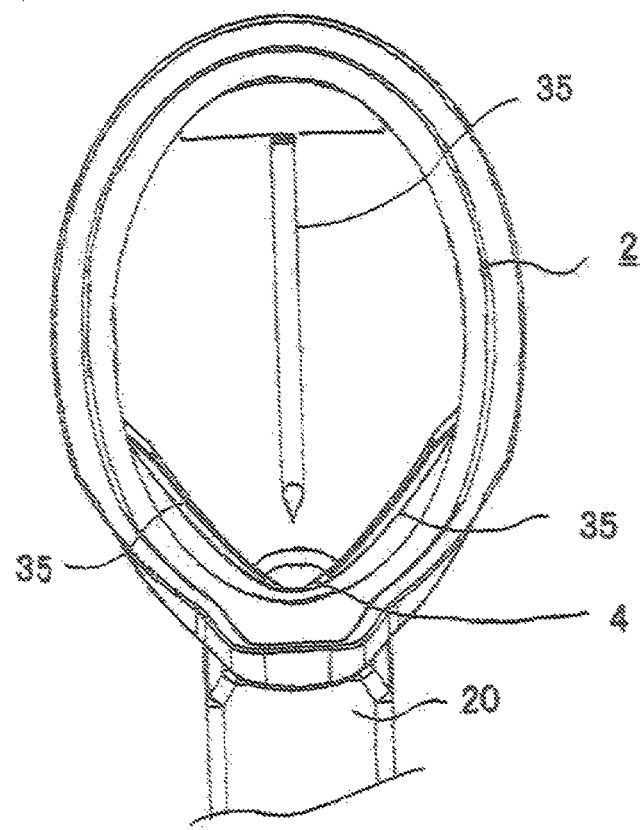
[Fig. 7b]
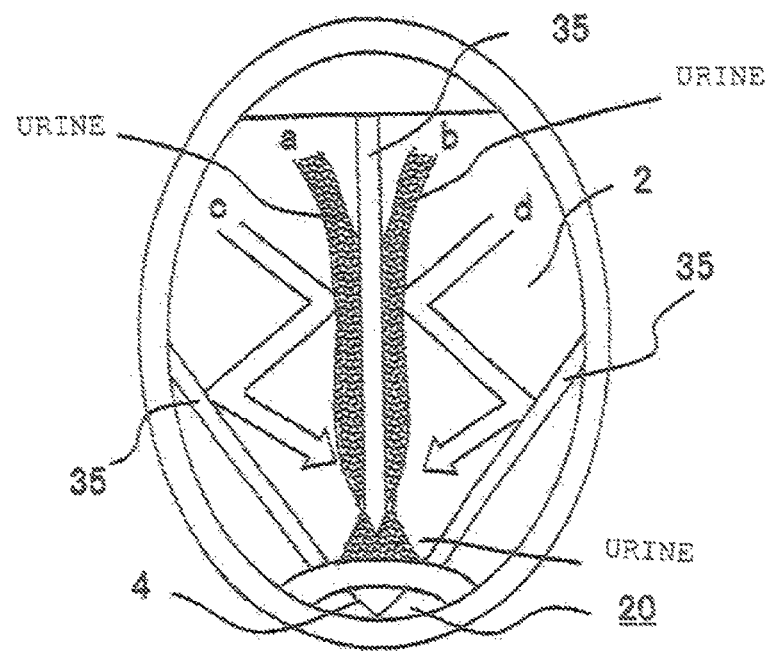

[Fig. 8a]
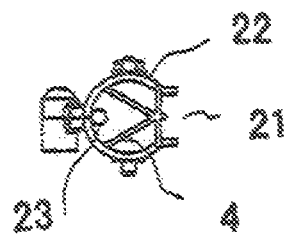
[Fig. 8b]
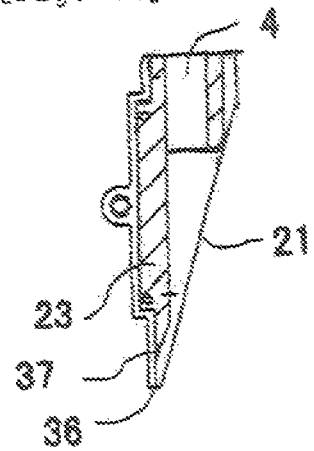
A-A SECTION
[Fig. 8c]
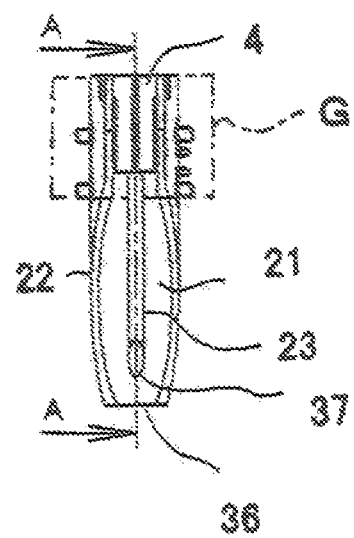

[Fig. 8d]
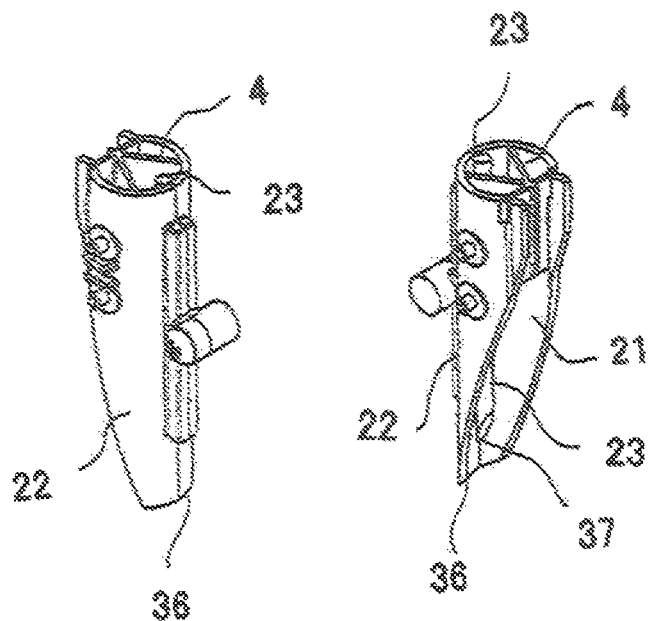
[Fig. 9a]
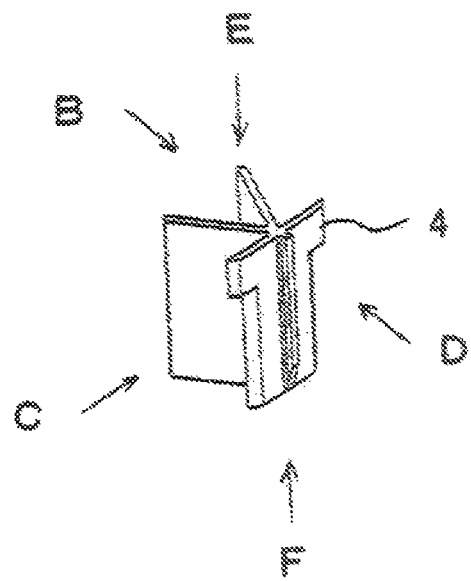

[Fig. 9b]
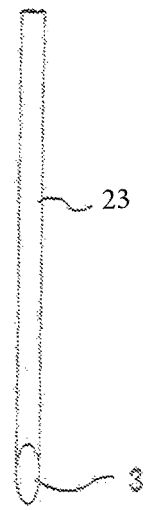
23
37
[Fig. 9c]
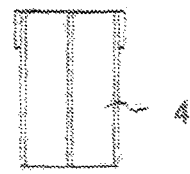
4
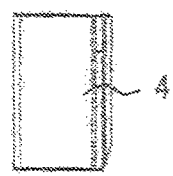
4
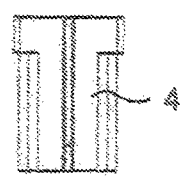
4
VIEW AS SEEN FROM
ARROW B DIRECTION
VIEW AS SEEN FROM
ARROW C DIRECTION
VIEW AS SEEN FROM
ARROW D DIRECTION
4
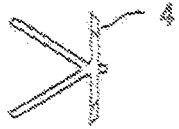
4
VIEW AS SEEN FROM
ARROW E DIRECTION
VIEW AS SEEN FROM
ARROW F DIRECTION

[Fig. 10a]
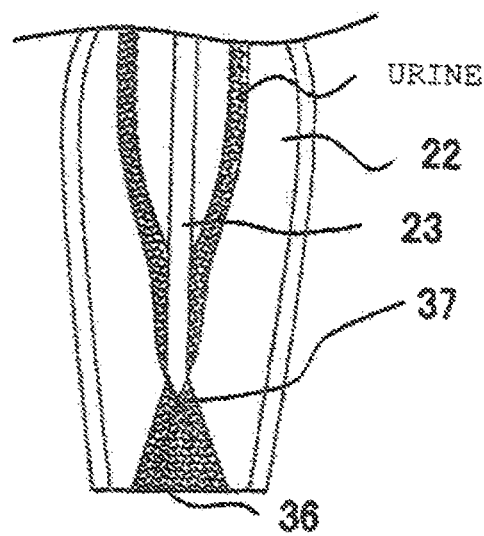
[Fig. 10b]
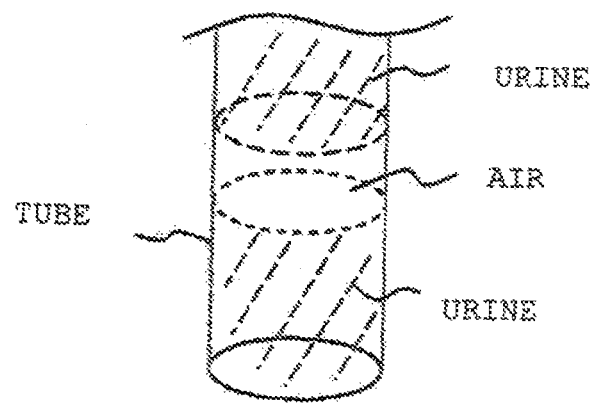

[Fig. 11]
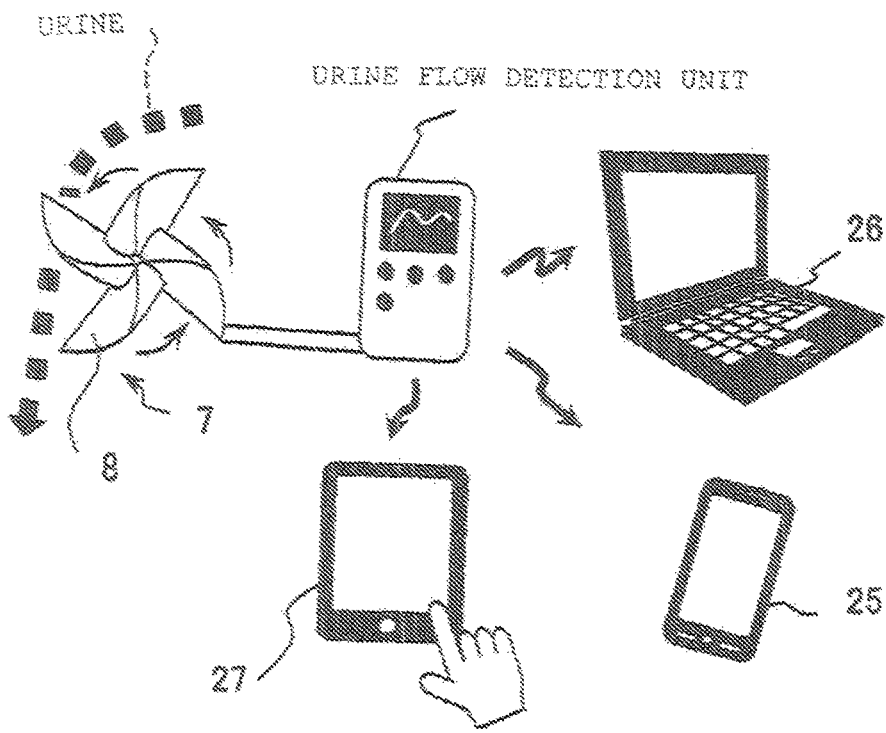
[Fig. 12a]
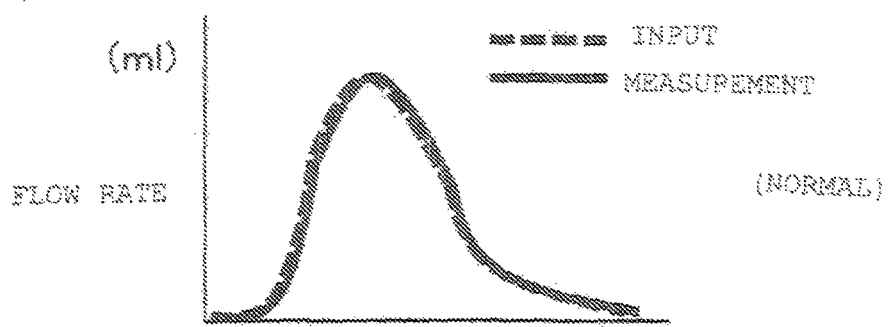
[Fig. 12b]
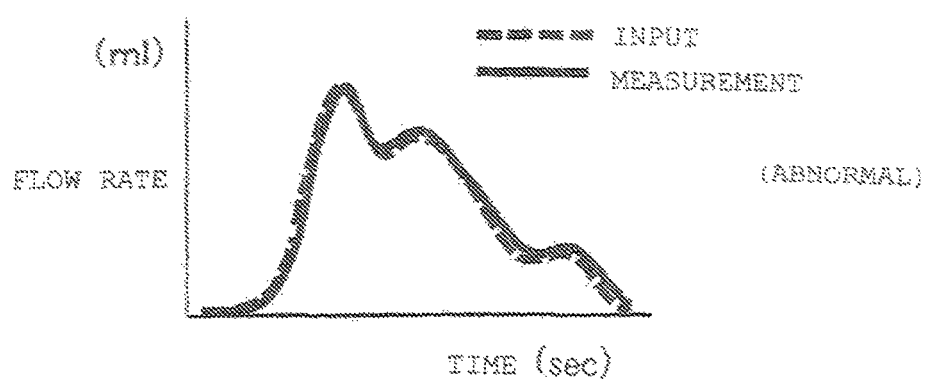

[Fig. 12c]
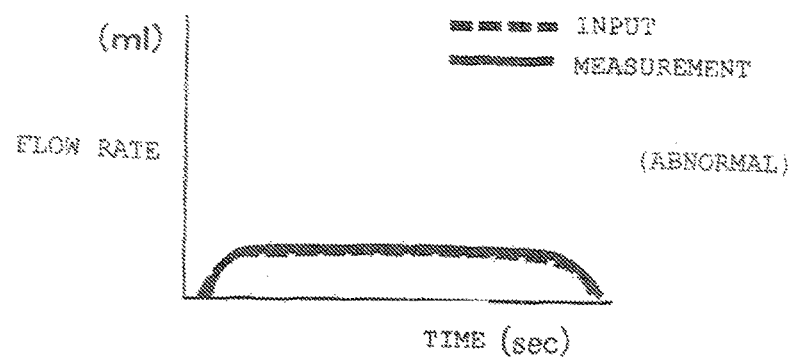
[Fig. 13]
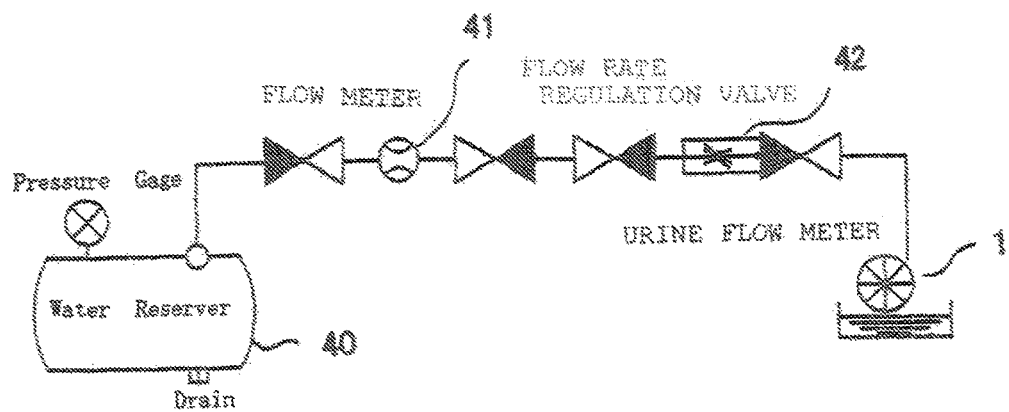

[Fig. 14]

PORTABLE URINE FLOW METER INCLUDING A GUIDE ARRANGED IN A NOZZLE PART IN A URINE FLOW PASSAGE TUBE

TECHNICAL FIELD

The present invention relates to a portable urine flow meter that can be easily used in home and the like.

BACKGROUND ART

It is said that there are over 20 million dysuria patients in an aging society. As causes of the dysuria, a disease in the urinary bladder, a disease in the male's prostate gland and the like may be exemplified. For example, it is said that there are over 4 million prostate gland-injured patients having prostate gland enlargement or the like.

For the patients having the dysuria due to the injury to the prostate gland, the urinary bladder or the like, it is very important therapeutically to perceive a state of urination and a state of a urine volume. Currently, as a method of perceiving the state of the urine volume, there is an outpatient test in a hospital, for example. Also, a method of collecting the urine into a receptacle each time urine is discharged and measuring a urine volume to perceive the state of the urine volume is used in home and the like.

CITATION LIST

Patent Literature

PTL 1: Patent 2009-084821
PTL 2: Patent 2007-108085

SUMMARY OF INVENTION

Technical Problem

However, it can be said that it is not possible to record 24-hours urination per a day at medical institutions/outpatient clinics. At current situations, the record is made by a single measurement. Also, in order to record the 24-hours urination per a day, a paper cup is used for measurement in home and the like. However, it causes problems of treatment of the used paper cup, mis-recording and the like. Further, when the paper cup is used, it is not possible to record information of a urination rate upon the urination and only a record of a total amount is obtained. As a result, upon diagnosis, a urination function is evaluated and diagnosed without a urination curve in the present circumstances.

The present invention is to easily measure and record a flow rate and a flow velocity in home and the like without collecting and accumulating urine in a receptacle upon urination and without the need for support of medical personnel. Also, the present invention is to easily acquire and record a 24-hours or 72-hours urination record, which has been acquired only under assistance of the medical personnel at medical institutions based on hospital admission, by recording time of occurrence at the same time.

Solution to Problem

In order to achieve the above objects, the present invention provides following configurations as means for solving the problems. That is, a urine flow meter of a first invention includes a urine collection part configured to collect urine to urinate and provided at one end-side of a urine flow passage tube through which the urine to be collected by the urine collection part is to flow. The other end-side of the urine flow passage tube is provided with a water wheel unit having a water wheel configured to rotate by flowing of the urine to flow from the urine flow passage tube and having a plurality of blades. The urine flow meter includes a rotation detection means configured to detect rotation of the blades. A shape of an end portion of the urine flow passage tube by which the urine is to be hit against the water wheel is formed so that a tip-side of the urine flow passage tube is acutely processed to form a nozzle part having an opening formed on a sidewall surface of the tip-side of the urine flow passage tube, a guide extending in a longitudinal direction of the nozzle part is provided in a urine flow passage between the opening of the nozzle part and an opposite sidewall surface thereto, a tip of the guide is disposed to extend to a tip-side region of the urine flow passage tube and is obliquely formed to have a tapered shape, the urine to flow through the urine flow passage tube is to be introduced into the nozzle part, is to be guided by the guide, is to be introduced into the tip of the guide, is to be collected at the tip-side of the guide and is to flow down to tip-sides of the blades to rotate the water wheel, the rotation of the wafer wheel is to be detected by the rotation detection means and a urine flow rate is to be detected on the basis of the rotation detection information.

In the urine flow meter of a second invention, in addition to the configuration of the first invention, an inner peripheral wall of the urine collection unit is provided with a rotational flow-down suppressing guide having at least one of a concave part and a convex part configured so that the urine to be collected is to flow down from an upper part-side of the inner peripheral wall toward a lower part-side thereof without rotational flow-down, is to be collected to a urine introduction port-side of the urine flow passage tube and is then to flow down.

In the urine flow meter of a third invention, in addition to the configuration of the first or second invention, a tip-side of the nozzle part is formed longer than the tip of the guide, a central portion of a peripheral wall of the longer part is formed with a urine ejection port and the ejection port is disposed to face a tip portion of the blade.

In the urine flow meter of a fourth invention, in addition to the configuration of the first or second invention, the rotation detection means is configured by a rotation detection sensor configured to detect the rotation information of the water wheel by using a composite magnetic wire configured to cause a large Barkhausen jump phenomenon.

A urine flow information detection system of a fifth invention is configured to transmit the rotation detection information, which is to be detected by the rotation detection means of the urine flow meter of the first invention, to a data processing device provided outside the urine flow meter, to enable the data processing device to calculate a urine flow rate and to automatically prepare a urination diary on the basis of detection time of the rotation detection information.

Advantageous Effects of Invention

The present invention has the urine collection part configured to collect the urine to urinate, the urine collection unit is provided at one end-side of the urine flow passage tube through which the urine collected by the urine collection part is to flow, and the water wheel unit is provided at the other end-side of the urine flow passage tube. The water wheel unit has the water wheel configured to rotate by the flowing of the urine to flow from the urine flow passage tube.

The shape of the end portion of the urine flow passage tube by which the urine is to be hit against the water wheel is formed so that the tip-side of the urine flow passage tube is acutely processed (obliquely cut) to form the nozzle part having the opening formed on the sidewall surface of the tip-side of the urine flow passage tube, and the urine is to flow from the tip-side of the nozzle part and is to be hit against the water wheel. The nozzle part having the above shape is provided at the tip-side of the urine flow passage tube, so that the urine smoothly flows and hits against the water wheel. That is, since the nozzle part is formed with the opening on the sidewall surface, the urine flows through the urine flow passage tube without an air layer and without being stagnant.

Also, the guide extending in the longitudinal direction of the nozzle part is provided in the urine flow passage between the opening of the nozzle part and the opposite sidewall surface thereto. The tip of the guide is disposed to extend to the tip-side region of the urine flow passage tube and is obliquely formed to have a tapered shape. For this reason, when the urine flowing through the urine flow passage tube is introduced into the nozzle part, the urine is led to the guide, is led to the tip of the guide, is collected at the tip-side of the guide and flows down toward the tip-side of the blade of the water wheel.

That is, according to the present invention, the urine to be collected by the urine collection part passes through the urine flow passage tube, is introduced into the nozzle part provided at the tip-side thereof and is led by the guide, so that the urine is enabled to hit against the tip of the blade of the water wheel at an appropriate state without turning (rotating). Then, the water wheel is rotated and the rotation of the water wheel is detected by the rotation detection means of the blade of the water wheel. Therefore, it is possible to correctly detect the urine flow information (flow velocity, flow rate and the like) on the basis of the rotation detection information. In this way, the present invention can correctly detect the urine flow rate with the simple configuration.

Also, according to the present invention, the inner peripheral wall of the urine collection part is provided with the rotational flow-down suppressing guide having at least one of the concave part and the convex part, so that following effects can be realized. That is, the rotational flow-down suppressing guide is formed so that the urine to be collected flows down from the upper part-side of the inner peripheral wall toward the lower part-side thereof without rotational flow-down, is collected to the urine introduction port-side of the urine flow passage tube and flows down. For this reason, when the rotational flow-down suppressing guide is provided, even though the momentum of the urine to urinate is weak, the urine flows down from the upper part-side toward the lower part-side without rotating, is collected to the urine introduction port-side of the urine flow passage tube and flows down. For this reason, the urine is correctly introduced into the urine flow passage tube, so that it is possible to correctly measure the urine flow rate.

Further, the tip-side of the nozzle part is formed longer than the tip of the guide, the central portion of the peripheral wall of the longer part is formed with the urine ejection port and the ejection port is disposed to face a tip portion of the blade. Thereby, following effects are realized. That is, the urine is led by the guide, is collected at the tip-side of the guide, is more correctly ejected from the central portion of the sidewall of the tip-side of the nozzle part (from the opposite side to the opening), as if is, and flows down toward the tip-side of the blade of the water wheel. For this reason, if is possible to more correctly detect the urine flow rate.

Also, the rotation detection means is configured by the rotation detection sensor configured to detect the rotation information of the water wheel by using a composite magnetic wire configured to cause a large Barkhausen jump phenomenon. Thereby, following effects are realized. That is, as the water wheel rotates, the rotation detection means having the above configuration can obtain a pulse voltage of a constant magnitude, irrespective of the rotating speed. Also, the rotation detection means having the above configuration can detect the rotation of extremely low speed. For this reason, the rotation detection means having the above configuration can securely measure even the urine flow of an extremely low flow rate, so that it is possible to correctly measure the urine flow rate.

Also, since the rotation detection means having the above configuration does not require a power supply, it can be applied as a sensor for which a power supply is not required, can be made small and can be easily performed in terms of maintenance. Therefore, the rotation detection means is configured by the rotation detection sensor configured to detect the rotation information of the water wheel by using the composite magnetic wire configured to cause a large Barkhausen jump phenomenon, so that it is possible to implement the urine flow meter having the above effects.

As described above, according to the urine flow meter of the present invention, whenever the user urinates, it is possible to easily measure the information such as the urine flow rate, the flow velocity of the urine and the like. Also, since the configuration is simple, it is possible to make the urine flow meter small and to manufacture the same at low cost. Also, according to the present invention, after the urine passes through the urine flow passage tube and hits against the water wheel, it is discharged outside (the collected urine is not reserved). Therefore, it is not necessary to make a clearance of the urine, unlike the device of the related art. For this reason, when the urine flow meter of the present invention is provided all the time in a house or institution of an aged person and the urine flow information is detected for a predetermined time period, it is possible to appropriately detect the urine flow information. As a result, it is possible to predict urination time, which may be helpful to nursing such as timely replacement of a diaper, support for a toilet and the like.

BRIEF DESCRIPTION OF DRAWINGS

FIG. 1 is a pictorial sectional view for illustrating an illustrative embodiment of a urine flow meter according to the present invention.

FIG. 2 is a pictorial side view for illustrating the urine flow meter of the illustrative embodiment.

FIG. 3 is a pictorial perspective view for illustrating the urine flow meter of the illustrative embodiment.

FIG. 4 is a pictorial sectional view for illustrating an example of a state where the urine flow meter of the illustrative embodiment is mounted to a toilet bowl.

FIG. 5 is a pictorial perspective view for illustrating an example of the state where the urine flow meter of the illustrative embodiment is mounted to the toilet bowl.

FIG. 6 is a pictorial view for illustrating a configuration of blades of a water wheel that is to be applied to the urine flow meter of the illustrative embodiment.

FIG. 7a is a pictorial plan view for illustrating a configuration of a urine collection part that is to be applied to the urine flow meter of the illustrative embodiment.

FIG. 7b is a pictorial view for illustrating a flow of water that is to be introduced from the urine collection part of the urine flow meter of the illustrative embodiment into a urine flow passage tube.

FIG. 8a is a pictorial plan view for illustrating a configuration of a nozzle part in which a blade-shaped partition plate to be applied to the urine flow meter of the illustrative embodiment is inserted and fixed.

FIG. 8b is a pictorial sectional view for illustrating the configuration of the nozzle part in which the blade-shaped partition plate to be applied to the urine flow meter of the illustrative embodiment is inserted and fixed.

FIG. 8c is a pictorial view for illustrating the configuration of the nozzle part in which the blade-shaped partition plate to be applied to the urine flow meter of the illustrative embodiment is inserted and fixed, as seen from an opening-side.

FIG. 8d is a pictorial perspective view for illustrating the configuration of the nozzle part in which the blade-shaped partition plate to be applied to the urine flow meter of the illustrative embodiment is inserted and fixed.

FIG. 9a is a pictorial perspective view for illustrating a configuration of the blade-shaped partition plate to be applied to the urine flow meter of the illustrative embodiment.

FIG. 9b is a pictorial perspective view for illustrating a configuration of a guide provided for the nozzle part to be applied to the urine flow meter of the illustrative embodiment.

FIG. 9c is a pictorial view for illustrating the configuration of the blade-shaped partition plate to be applied to the urine flow meter of the illustrative embodiment, as seen from an arrow direction.

FIG. 10a is a pictorial view for illustrating a flow of water that is to pass through the nozzle part of the urine flow meter of the illustrative embodiment and is to be ejected to the water wheel.

FIG. 10b is a pictorial view for illustrating an example of a state where an air layer is formed when urine is introduced into a tube passage (tube) having no opening.

FIG. 11 is a pictorial image view for illustrating a data analysis system using the urine flow meter.

FIG. 12a is a graph depicting a temporal change of a urine flow rate (water flow rate) of a normal person, which is detected using the urine flow meter of the illustrative embodiment, and a change of an actual urine flow rate (water flow rate).

FIG. 12b is a graph depicting a temporal change of a urine flow (quantity of water flow) of a person having a disease, which is detected using the urine flow meter of the illustrative embodiment, and a change of an actual urine flow (quantity of water flow).

FIG. 12c is a graph depicting a temporal change of a urine flow (quantity of water flow) of a person having a disease different from the example of FIG. 12b, which is detected using the urine flow meter of the illustrative embodiment, and a change of an actual urine flow (quantity of water flow).

FIG. 13 is a pictorial view depicting an example of a method for comparing and measuring a urine flow (quantity of water flow), which is detected using the urine flow meter of the illustrative embodiment, and a change of an actual urine flow (quantity of water flow).

FIG. 14 illustrates an example of a urination diary prepared by a data processing device.

DESCRIPTION OF EMBODIMENTS

Hereinafter, an illustrative embodiment of the present invention will be described with reference to the drawings.

EXAMPLE(S)

FIG. 1 is a pictorial sectional view depicting a configuration of main parts of an illustrative embodiment of a urine flow meter according to the present invention, and FIG. 2 is a pictorial side view thereof. Also, FIG. 3 is a pictorial perspective view depicting the configuration of main parts of the urine flow meter in accordance with the illustrative embodiment. In the meantime, in FIG. 1 to FIG. 3, some of the configuration of a urine flow meter 1 are omitted, and FIG. 2 is a side view as seen from an S direction of FIG. 3.

As shown in FIG. 1, the urine flow meter 1 of the illustrative embodiment has a urine collection part 2 configured to collect urine to urinate and a urine flow passage tube 20 through which the urine to be collected by the urine collection part 2 is to flow. The urine collection part 2 is provided at one end-side of the urine flow passage tube 20. As shown in FIG. 1 to FIG. 3, a urine entrance-side of an upper end-side of the urine collection part 2 has a curved shape (curved surface shape) so that it is disposed in the vicinity of a user's urination organ in a familiar aspect with the urination organ. The urine collection part 2 having such a shape is configured to collect urine with being fitted in the vicinity of the urination organ (a urine discharging part). That is, the urine collection part has a shape capable of easily collecting the urine, irrespective of whether the user is a male or a female, so that it is possible to prevent the urine from being splashed.

That is, as shown in FIG. 4, for example, the illustrative embodiment is to be used with being attached to a toilet bowl 9, and the urination at a sitting posture is made at a state where a user's posture is defined. Regarding this, the urine collection part 2 has the curved shape, so that it is possible to dispose the urine collection part 2 in the vicinity of the urination organ (or to bring the urine collection part into contact with the urination organ) to be fitted to the user's urination organ.

As shown in FIG. 1 and FIG. 4, the other end-side of the urine flow passage tube 20 is provided with a water wheel unit 6. The water wheel unit 6 has a water wheel 7 configured to rotate by a flow of the urine flowing from the urine flow passage tube 20. A size of the water wheel is 30 mmϕ, for example, and the water wheel 7 has a plurality of (eight, in this illustrative embodiment) blades 8. The blade 8 is made of plastic such as PEEK (polyether ether ketone), for example.

As shown in FIG. 6, tip-sides of the blades 8 are provided with magnets 13 with being embedded in the blades 8. The magnets 13 are provided at positions equally spaced outward from a center of the water wheel 7. Also, in the illustrative embodiment, as a bearing of the water wheel 7, a ball bearing is adopted and has a following configuration. In the meantime, since the configuration where the ball bearing is used as the bearing is well known, it is not shown in a view for illustrating the configuration of the water wheel 7 and the bearing is not particularly illustrated in the drawings.

Also, when disposing a bearing of $\Phi D$ mm over a total extension L of a circumferential bearing groove, if the number of the bearings to be disposed is denoted with N, N is expressed by N=INT(L/D). In the meantime, INT is an INT function, which is to truncate a number after the decimal point of a quotient of L/D. In the urine flow meter 1 of the illustrative embodiment, the (N−1) bearings are to be mounted. This is to generate rotation of the bearing and to move the bearing in a circumferential direction of the bearing groove when the blades 8 are rotated by wafer flow. That is, a void is generated by shortening an occupying length of the bearing (an occupying length in the circumferential direction of the bearing groove) relative to a circumferential length of the bearing groove. By the void, the bearing is enabled to freely move in the circumferential direction to some extent, so that the bearing can rotate and move in the circumferential direction.

For this reason, even when impurities and the like included in the urine are crystallized, the crystallized impurities and the like can be crushed by movement of the bearings. Therefore, in the illustrative embodiment, it is possible to solve an increase in frictional resistance, which is to be caused due to attachment of urinary calculi and the like to a shaft part of the water wheel 7. Also, according to the illustrative embodiment, it is possible to crush the impurities and the like by movement of the bearings, so that it is possible to perform cleaning and sterilization by circulating a cleaning liquid and a disinfectant solution. That is, it is possible to implement a more sanitary device.

Also, the water wheel unit 6 of the urine flow meter 1 of the illustrative embodiment is provided with a rotation detection means configured to detect the rotation of the water wheel 7. The rotation detection means is configured by a rotation detection sensor (coil) 3 provided at an outer side of the water wheel 7 in the water wheel unit 6 with being spaced from the water wheel 7. The rotation detection sensor 3 is provided at a position facing the magnet 13, and is configured by a sensor configured to detect rotation information of the water wheel 7 by using a composite magnetic wire configured to cause a large Barkhausen jump phenomenon.

As shown in FIG. 1, FIG. 3, FIG. 7a and FIG. 7b, an inner peripheral wall of the urine collection part 2 is provided with a rotational flow-down suppressing guide 35 configured by a convex part. A tip portion of the rotational flow-down suppressing guide 35 formed at a center is obliquely formed to have a tapered shape and is disposed at a space from a urine introduction port of the urine flow passage tube 20. The rotational flow-down suppressing guide 35 is provided so that the urine to be collected is to flow down from an upper part-side toward a lower part-side of the inner peripheral wall without rotational flow-down (without forming a turbulent flow), is to be collected to the urine introduction port-side of the urine flow passage tube 20 and is then to flow down.

FIG. 7b is a pictorial image view depicting a flow-down situation of the urine to be introduced info the urine collection part 2. As shown, when the urine is introduced into the urine collection part 2, the urine introduced to positions denoted with a and b in FIG. 7b, for example, flows down along the central rotational flow-down suppressing guide 35. Also, the urine introduced to positions denoted with c and d in FIG. 7b flows down as shown with arrows, hits against the rotational flow-down suppressing guide 35 and then flows down along the central rotational flow-down suppressing guide 35. In any case, the urine is collected at a tip-side of the central rotational flow-down suppressing guide 35, flows down along the tapered shape of the tip portion and is then introduced into the urine flow passage tube 20 with flowing along an inner wall of the urine flow passage tube 20. That is, even when the urine is introduced at any direction and angle of the urine collection part 2, the urine is forcibly enabled to vertically flow down, so that the urine is introduced into the urine flow passage tube 20 substantially around the same time.

Also, in the illustrative embodiment, as shown in FIG. 1, a tip portion (an end portion for enabling the urine to hit against the water wheel 7) of the urine flow passage tube 20 has a characteristic shape. That is, a tip-side of the urine flow passage tube 20 is acutely processed (one side of the tip-side is obliquely cut) to form a nozzle part 22 having an opening 21 formed on a sidewall surface. A blade-shaped partition plate 4 is inserted and fixed in the nozzle part 22. In the below, configurations and a fixing structure of the nozzle part 22 and the blade-shaped partition plate 4 are described with reference to FIG. 8a to FIG. 8d and FIG. 9a to FIG. 9c.

As shown in FIG. 8a to FIG. 8d, the nozzle part 22 is formed by obliquely cutting the tip-side of the urine flow passage tube 20 having a substantially circular section. An inner diameter of an upper end-side of the urine flow passage tube 20 is 10 mmφ, and a length from the upper end of the urine flow passage tube 20 to the tip (lower end) is 40 mm, for example. A region G of FIG. 8c indicates a region in which a peripheral wall of the urine flow passage tube 20 is vertically cut along a longitudinal direction of the urine flow passage tube 20 from the upper end of the urine flow passage tube 20 to a lower side of about 10 mm. In this region, as shown in FIG. 9a and FIG. 9c, the blade-shaped partition 4 having a length (a length in a height direction) of about 10 mm is provided and forms an aspect as shown in FIG. 8a to FIG. 8d. In the meantime, the blade-shaped partition plate 4 has four plates, in this illustrative embodiment, and two plates facing the opening 21 have an upper end-side more protruding than a lower end-side, respectively.

Also, a guide 23 as shown in FIG. 9b extends in the longitudinal direction of the nozzle part 22 in a urine flow passage between the opening 21 of the nozzle part 22 and an opposite sidewall surface thereto (refer to FIG. 1 and FIG. 8b to FIG. 8d). A tip 37 of the guide 23 is obliquely formed to have a tapered shape and is disposed to extend to the tip-side region of the nozzle part 22. Although a diameter and a length of the guide 23 are not particularly limited, a diameter of the guide 23 is formed to be about 2 mmφ to 3 mmφ and a length thereof is formed shorter than the tip of the nozzle part 22. That is, in the illustrative embodiment, the tip-side of the nozzle part 22 is formed longer than the tip of the guide 23, a central portion thereof is formed with a urine ejection port 36, and the urine ejection port 36 (urine flowing-down entrance) is made to face the tip portion of the blade 8.

In the meantime, the peripheral wall of the nozzle part 22 formed longer than the guide 23 may have an arc shape of which a diameter decreases (a shape of which a tip portion is round), and a central portion of the arc-shaped diameter-decreasing part may be configured as the urine ejection port 36. Also, ejection (flowing down) of the urine from the urine ejection port 36 may be favorably performed.

The nozzle part 22 is formed with the opening 21, so that it is possible to realize following effects. That is, for example, as shown in FIG. 10b, when a general tube having no opening is vertically disposed and the urine is enabled to pass therethrough, an air layer tends to be generated. However, since the urine flow passage tube 20 of the illustrative embodiment forms the nozzle part 22 having the opening 21 formed on a side surface, when the urine flows therethrough, an air layer is not formed. That is, the opening 21 provides an effect of preventing a situation where an air layer is formed to block the smooth flow down of the urine. Also, the nozzle part 22 is provided with the blade-shaped partition 4, so that it is possible to prevent a turbulent flow of the flowing down urine and to make the flowing down of the urine smoother.

As shown in FIG. 10a, the urine flowing through the urine flow passage tube 20 is introduced into the nozzle part 22, is guided by the guide 23, is led to the tip 37 of the guide 23, is collected to the tip-side of the guide 23 and flows down from the ejection port 36 of the nozzle part 22 toward the tip-side of the blade 8 of the water wheel 7 (flows downs without rotating). That is, the urine is guided and collected to the guide 23, becomes small by surface tension (with being collected), and is then hit against the tip portion of the blade 8 vertically or substantially vertically, which faces the tip of the nozzle part 22, from the tip (urine ejection port) 36 of the nozzle part 22.

Meanwhile, in the illustrative embodiment, there is also urine that is directly hit against the water wheel 7 without being guided by the guide 23 of the nozzle part 22. However, the urine is also hit against the tip-side of the blade 8 of the water wheel 7. The reason is that when the urine flow meter 1 of the illustrative embodiment is attached to the toilet bowl 9, it is disposed so that an angle between the opening 21 of the nozzle part 22 and a floor surface (an Ax direction in FIG. 4) is vertical or substantially vertical, as shown in FIG. 4. The substantially vertical angle is an angle within a range in which an angle difference from the vertical angle is about 0° to 15°.

When the urine flow meter is disposed so that the angle between the opening 21 of the nozzle part 22 and the floor surface (an Ax direction in FIG. 4) is vertical or substantially vertical, the urine, which is to be directly hit against the water wheel 7 without being guided by the guide 23 due to high momentum, is appropriately directly hit against the tip portion of the blade 8 of the water wheel 7 at the vertical or substantially vertical angle. Also, the urine flowing down along the peripheral wall of the nozzle part 22, guided by the guide 23, ejected (flowing down) from the ejection port 36 of the tip of the nozzle part 22 and then hit against the water wheel 7 is also appropriately hit against the tip portion of the blade 8 of the water wheel 4. That is, in any case, the urine is appropriately hit against the tip portion of the blade 8 of the water wheel 7 in a pinpoint manner.

The urine is hit against the water wheel 7, so that the water wheel 7 is rotated, the rotation of the water wheel 7 is detected by the rotation detection means and a urine flow is detected on the basis of the rotation detection information. That is, the gravity acceleration of the urine collected at the urine collection part 2 and passing through the urine flow passage tube 20 is converted into an angular acceleration of rotation of the water wheel 7 and a pulse is generated by the rotation of the water wheel 7. Therefore, the generated pulse is detected by the rotation detection sensor 3, so that the rotation of the water wheel 7 is detected and a urine flow rate is detected on the basis of the rotation information. The urine is discharged from a discharge port 30.

In the illustrative embodiment, since the rotation detection means is configured by the sensor configured to detect the rotation information of the water wheel 7 by using the composite magnetic wire configured to cause a large Barkhausen jump phenomenon, the generation of pulse resulting from the rotation of the water wheel 7 and the detection thereof are made as described above.

Meanwhile, in the illustrative embodiment, the magnets 16 configured to function as a set magnetic field and the magnets 18 configured to function as a reset magnetic field are alternately disposed for the water wheel 7 having the eight blades (blades 8), as shown in FIG. 6. That is, the four magnets are alternately disposed every 90° with a magnetic field direction being reversed. The number of pulses counted by the rotation detection means (the rotation detection sensor 3) is stored in a memory of a measurement unit 31, which is arranged outside the toilet bowl 9, together with time of occurrence, as shown in FIG. 4 and FIG. 5. The stored urination information is transmitted to an external data processing device (HOST device) having a data processing function.

The external data processing device (HOST device) is a reception unit of an appropriate device having an information analysis function, such as a smart phone 25, a PC 26, a wireless tablet terminal 27 and the like, as shown in an image view of FIG. 11. The external data processing device is configured to calculate rotating speed and rotational acceleration of the water wheel 7 from the pulses on the basis of the transmitted data and to calculate a flow rate on the basis of inertia moment and the like of the water wheel 7. In the meantime, the measurement unit 31 is preferably configured to input the information from the rotation number detection means of the water wheel 7 into the memory. Therefore, the measurement unit may be provided on a wall of toilet room or in a pocket of a measurer of the urine flow inasmuch as it is electrically connected to a main body of the urine flow meter 1 by a communication line, without being limited to the attachment to the toilet bowl 9.

In the illustrative embodiment, when calculating the urine flow rate from the rotation information of the water wheel 7, it may be calculated by performing appropriate idling correction on the basis of a calculation method or data calculation information prepared in advance, for example. For example, in the illustrative embodiment, a urine flow rate per unit time (ml/sec) is obtained and a correct urine flow rate (flow velocity of urine) per urine flow unit time is obtained.

As described above, according to the illustrative embodiment, the configuration of the urine collection part 2, the configuration of the nozzle part 22, the arrangement configuration of the urine flow meter 1 are made to have the above-described features. Thereby, it is possible to correctly rotate the water wheel 7 with simple configuration, irrespective of whether the urination is fast or slow. The rotations are counted with pulses, which are then converted into the flow rate. Thereby, the urine flow meter 1 of the illustrative embodiment can detect the correct urine flow rate (flow velocity).

FIG. 12a to FIG. 12c depict data examples of measured values (measurement) measured with respect to normal and abnormal (person having a disease) urine flow rate patterns and actual urine flow rate (input). The example shown in FIG. 12a depicts a data example of a urine flow rate pattern of a normal person. The example shown in FIG. 12b depicts a urine flow rate data example of a person having bladder neck contracture or chronic prostatitis. The example shown in FIG. 12c indicates a urine flow rate data example of a person having prostate gland enlargement or urethral stenosis. As shown, the actually measured values (input) and the measured values substantially coincide with each other. That is, it can be seen that the measurement of the illustrative embodiment is correct. Also, the urine flow meter 1 of the illustrative embodiment has the simple configuration, is small and can be manufactured at low cost.

In the meantime, the data shown in FIG. 12a to FIG. 12c was obtained using a urination simulation system shown in FIG. 13, for example, as follows. Water is led from a pressure water tank 40 (water is led from the water tank 40 by applying a pressure to water in the water tank), instead of the urine, and the water is introduced into the urine collection part 2 of the urine flow meter 1 of the illustrative embodiment through a flow meter 41 and a proportional valve 42. At this time, the proportional valve 42 is opened for predetermined time (second) by a predetermined valve opening amount from a completely closed state on the basis of a predetermined pattern. Then, a value obtained by the flow meter 41 is set to an actual input amount, which is compared to a measured value measured by the urine flow meter 1.

As described above, according to the illustrative embodiment, it is possible to correctly measure the data of the urine flow rate by the urine flow meter 1. Therefore, for example, a urine flow meter-side data determination system may be provided for the appropriate device having an information analysis function such as the smart phone 25, the PC 26 and the like as shown in the pictorial view of FIG. 11.

Figure 14:
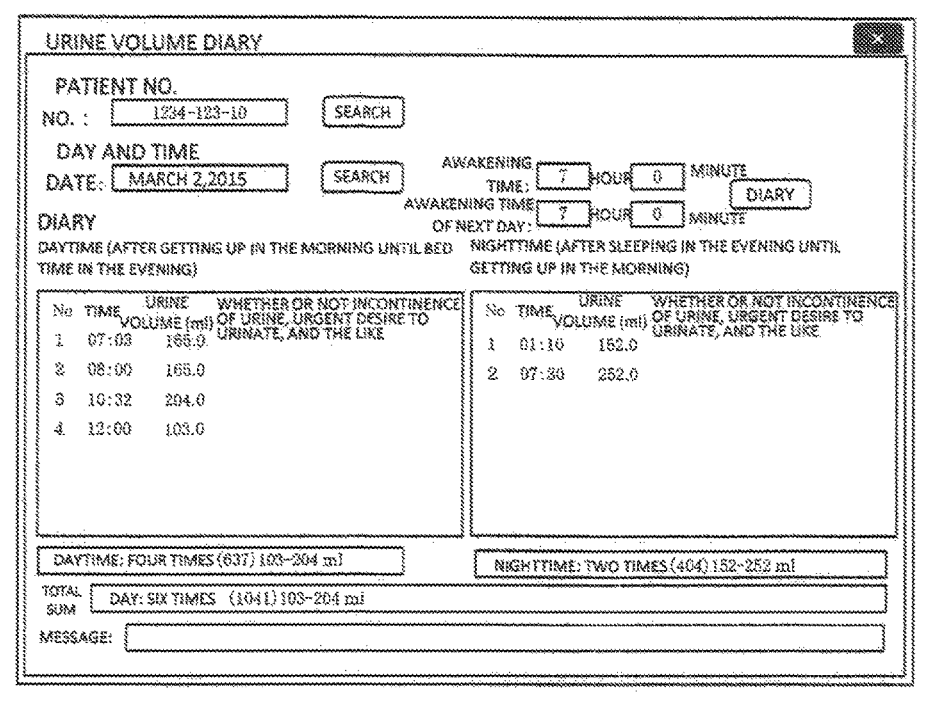

As described above, the data, which is to be stored in the memory of the measurement unit 31, is stored every urination together with time of occurrence, for example. Therefore, an awakening hour and a bedtime hour are separately set in the data processing device to which the data is to be transmitted, and the data processing device may be configured to automatically form a urination diary every year, month and day. By the system, the stored data further contributes to the provision of diagnosis information. FIG. 14 depicts an example of the urination diary.

Also, when the system as described above is provided, it is possible to prepare a diagnosis guideline about symptoms and diseases and to make applications thereof (for example, applications to treatment of a disease, nursing and the like). For example, the patterns of the urine flow rate data examples as shown in FIG. 12*a* to FIG. 12*c* are accumulated in advance, and the data examples are compared to temporal urine flow rate graphs prepared on the basis of data obtained by the urine flow meter 1. By doing so, it is possible to prepare a diagnosis guideline about symptoms and diseases.

Meanwhile, in the illustrative embodiment, the measurement unit 31 is configured to be freely detachable to the main body of the urine flow meter 1 shown in FIG. 1. For example, the measurement unit 31 and a main body holding part 32 are fixedly disposed at the toilet bowl 9, and the main body of the urine flow meter 1 is slid from above and fitted to a connection part 33 fixed to the main body holding part 32. By doing so, the connection part 33 of the measurement unit 31 and a connection part 34 of the main body of the urine flow meter 1 are mechanically connected, and the measurement unit 31 and the main body of the urine flow meter 1 are electrically connected.

Also, in the illustrative embodiment, when connecting the measurement unit 31 and the main body of the urine flow meter 1, a height position of the main body of the urine flow meter 1 can be changed in three steps, for example. By this configuration, since it is possible to stepwise vary an attachment height of the urine flow meter 1, it is possible to adjust the attachment height of the urine flow meter 1 in accordance with a body shape and a taste of the user, so that it is possible to favorably collect the urine. In the meantime, the height adjusting configuration is not particularly limited and may be omitted. Also, the height may be adjusted in two steps or four or more steps or may be continuously adjusted.

Also, according to the urine flow meter 1 of the illustrative embodiment, after discharging the urine into the urine flow meter 1, when the main body of the urine flow meter 1 is detached from the connection part 33 and is dropped into the toilet bowl 9 and an interior of the toilet bowl 9 is flushed, it is possible to automatically clean the main body of the urine flow meter 1 by the water (both the toilet bowl and the urine flow meter 1 are cleaned by the water for flushing the toilet bowl). In the meantime, when dropping the urine flow meter 1 into the toilet bowl 9, the urine flow meter 1 is dropped with a string, a cord or the like being connected to a handle part 24 of the urine flow meter 1. This configuration is preferable because it is possible to easily pull up the cleaned urine flow meter 1 from the inside of the toilet bowl 9.

The present invention is not limited to the above illustrative embodiment and can be implemented in various forms without departing from the technical scope of the present invention. That is, the present invention is configured by diversely combining the respective constitutional parts of the illustrative embodiment. In the below, additional illustrative embodiments are described. However, illustrative embodiments that are not to be included in the corresponding description can also be implemented in various forms without departing from the technical scope of the present invention, for example, by diversely combining the configurations of the claims.

For example, in the above illustrative embodiment, as the rotation detection means configured to detect the rotation of the water wheel 7, the rotation detection sensor 3 using the composite magnetic wire configured to cause a large Barkhausen jump phenomenon has been adopted. However, the rotation detection means is not particularly limited and is appropriately composed. For example, a variety of sensors such as sensors using diverse proximity switches and Hall elements can also be applied.

Also, the diameters and lengths of the urine flow passage tube 20 and the nozzle part 22 are not limited and are appropriately composed. That is, the urine flow passage tube 20 having a urine flow passage through which the urine can flow without being stagnant may be provided and a tip-side thereof may be provided with the nozzle part 22 of the illustrative embodiment. In the meantime, the nozzle part 22 is provided with the opening 21 and the guide 23.

Further, in the above illustrative embodiment, the urine collection part 2 is provided with the rotational flow-down suppressing guide 35 having a convexed shape. However, the rotational flow-down suppressing guide 35 may also be formed by a concave part, and the rotational flow-down suppressing guide 35 may be omitted. However, the rotational flow-down suppressing guide 35 is preferably provided. Also, the shape and size of the urine collection part 2 of the urine flow meter 1 are not particularly limited, and are appropriately composed so as to appropriately collect the urine to be discharged from the user's urination organ.

Further, the water wheel 7 of the water wheel unit 6 to be applied to the urine flow meter 1 is not limited to the above illustrative embodiment, and the number, size, shape and the like of the blades 8 are appropriately composed.

Further, upon the measurement of the urine flow rate by using the urine flow meter 1 of the illustrative embodiment, the urine flow meter can also be applied when a male urinates in the standing position. When using the urine flow meter in the standing position of the male, the arrangement space upon using the urine flow meter 1 is less limited than in the sitting position. For this reason, even when the urine flow meter 1 is used in the standing position of the male, it is possible to correctly detect the urine flow rate if the urine collection part 2 is disposed in the vicinity of the urination organ (or is disposed to contact the urination organ) so as to be fitted to the user's urination organ, like the using in the sitting position.

Further, in the above illustrative embodiment, the measurement unit 31 is configured to store the rotation information of the water wheel 7 in the memory and to transmit the information toward the outside reception unit. However, the measurement unit 31 may be provided with a function of detecting the urine flow information on the basis of the rotation information of the water wheel 7. In the meantime, the urine flow information is not limited to the graphed information, and may be table information or numerated information. That is, the aspect of the urine flow information may be any aspect inasmuch as the urine flow rate and the total urine volume can be obtained.

INDUSTRIAL APPLICABILITY

According to the present invention, since it is possible to easily measure the flow rate and flow velocity of the urine in home and the like without collecting the urine in the receptacle upon the urination and to repeatedly perceive the urination state and the urine volume with ease, it is possible to use the present invention for detection of urination diseases and the like.

REFERENCE SIGNS LIST

1 urine flow meter
2 urine collection part
3 rotation detection sensor
4 blade-shaped partition
6 water wheel unit
7 water wheel
8 blade
13 magnet
15 magnetic wire
20 urine flow passage tube
21 opening
22 nozzle part
23 guide
35 rotational flow-down suppressing guide
36 urine ejection port (tip of nozzle part)
37 tip

The invention claimed is:

1. A urine flow meter comprising:
a urine collection part configured to collect urine to urinate and provided at one end-side of a urine flow passage tube through which the urine to be collected by the urine collection part is to flow;
a water wheel unit provided at the other end-side of the urine flow passage tube and having a water wheel configured to rotate by flowing of the urine to flow from the urine flow passage tube and having a plurality of blades, and
a rotation detection means configured to detect rotation of the blades,
wherein a shape of an end portion of the urine flow passage tube by which the urine is to be hit against the water wheel is formed so that a tip-side of the urine flow passage tube is acutely processed to form a nozzle part having an opening formed on a sidewall surface of the tip-side of the urine flow passage tube,
wherein a guide extending in a longitudinal direction of the nozzle part is provided in a urine flow passage between the opening of the nozzle part and an opposite sidewall surface thereto and a tip of the guide is disposed to extend to a tip-side region of the urine flow passage tube and is obliquely formed to have a tapered shape, and
wherein the urine to flow through the urine flow passage tube is to be introduced into the nozzle part, is to be guided by the guide, is to be introduced into the tip of the guide, is to be collected at the tip-side of the guide and is to flow down to tip-sides of the blades to rotate the water wheel, the rotation of the water wheel is to be detected by the rotation detection means and a urine flow rate is to be detected on the basis of the rotation detection information.

2. The urine flow meter according to claim 1, wherein an inner peripheral wall of the urine collection part is provided with a rotational flow-down suppressing guide having at least one of a concave part and a convex part configured so that the urine to be collected is to flow down from an upper part-side of the inner peripheral wall toward a lower part-side thereof without rotational flow-down, is to be collected to a urine introduction port-side of the urine flow passage tube and is then to flow down.

3. The urine flow meter according to claim 2, wherein a tip-side of the nozzle part is formed longer than the tip of the guide, a central portion of a peripheral wall of the longer part is formed with a urine ejection port, and the ejection port is disposed to face a tip portion of the blade.

4. The urine flow meter according to claim 2, wherein the rotation detection means is configured by a rotation detection sensor configured to detect the rotation information of the water wheel by using a composite magnetic wire configured to cause a large Barkhausen jump phenomenon.

5. The urine flow meter according to claim 1, wherein a tip-side of the nozzle part is formed longer than the tip of the guide, a central portion of a peripheral wall of the longer part is formed with a urine ejection port, and the ejection port is disposed to face a tip portion of the blade.

6. The urine flow meter according to claim 1, wherein the rotation detection means is configured by a rotation detection sensor configured to detect the rotation information of the water wheel by using a composite magnetic wire configured to cause a large Barkhausen jump phenomenon.

7. A urine flow information detection system configured to transmit rotation detection information, which is to be detected by the rotation detection means of the urine flow meter according to claim 1, to a data processing device provided outside the urine flow meter, to enable the data processing device to calculate a urine flow rate and to automatically prepare a urination diary on the basis of detection time of the rotation detection information.

* * * * *